United States Patent
Dayton

(10) Patent No.: US 10,369,243 B2
(45) Date of Patent: Aug. 6, 2019

(54) PHOTOCHROMIC INDICATOR AND A METHOD OF DOCUMENTING DECONTAMINATION OF AN OBJECT USING A PHOTOCHROMIC INDICATOR

(71) Applicant: Diversey, Inc., Charlotte, NC (US)

(72) Inventor: Roderick M. Dayton, Strongsville, OH (US)

(73) Assignee: Diversey, Inc., Charlotte, NC (US)

( * ) Notice: Subject to any disclaimer, the term of this patent is extended or adjusted under 35 U.S.C. 154(b) by 0 days.

(21) Appl. No.: 15/209,054

(22) Filed: Jul. 13, 2016

(65) Prior Publication Data

US 2017/0157279 A1  Jun. 8, 2017

Related U.S. Application Data

(60) Provisional application No. 62/263,864, filed on Dec. 7, 2015.

(51) Int. Cl.
*G01T 1/04* (2006.01)
*A61L 2/28* (2006.01)
(Continued)

(52) U.S. Cl.
CPC ........ *A61L 2/28* (2013.01); *A61L 2/10* (2013.01); *G03C 1/733* (2013.01); *A61L 2202/25* (2013.01)

(58) Field of Classification Search
CPC ........... A61L 2202/121; A61L 2202/14; A61L 2202/24; A61L 2/10; A61L 2/24;
(Continued)

(56) References Cited

U.S. PATENT DOCUMENTS 6,045,282 A * 4/2000 Begin ............... B05C 17/0308
401/197
6,322,416 B1* 11/2001 Burke ..................... A63H 33/22
446/175
(Continued)

FOREIGN PATENT DOCUMENTS

WO     2015184190 A1    12/2015

OTHER PUBLICATIONS

PCT International Search Report and Written Opinion From PCT International Application No. PCT/US2016/065233, International Filing Date Dec. 7, 2016 dated Feb. 17, 2017 (9 pgs).

*Primary Examiner* — Kiho Kim
(74) *Attorney, Agent, or Firm* — Kilpatrick Townsend & Stockton LLP

(57) ABSTRACT

Provided is a method and an apparatus for indicating minimum exposure of a surface to UVC light emitted by a source during a decontamination process to achieve a desired level of pathogen reduction. The apparatus includes a photochromic material to be applied to, or applied adjacent to the surface. The photochromic material is to exhibit a visible response to receiving the minimum exposure to the UVC light, and exhibit the visible response to a lesser extent after the photochromic material ceases to be exposed to the UVC light emitted by the source. A protective layer of material that is substantially transparent to the UVC light emitted by the source is positioned over the photochromic material to be disposed between the source and the photochromic material during the decontamination process.

13 Claims, 3 Drawing Sheets

(51) Int. Cl.
*A61L 2/10* (2006.01)
*G03C 1/73* (2006.01)

(58) Field of Classification Search
CPC ..... A61L 2/28; A61L 2202/25; G01N 31/226; G01N 31/229; G03C 1/733
USPC ...................................................... 250/473, 1
See application file for complete search history.

(56) References Cited

U.S. PATENT DOCUMENTS

| | | | | |
|---|---|---|---|---|
| 6,359,150 B1* | 3/2002 | Fukudome | ............... | C09K 9/02 548/517 |
| 6,437,346 B1* | 8/2002 | Goudjil | .................. | G01J 1/50 250/372 |
| 6,475,433 B2 | 11/2002 | McGeorge et al. | | |
| 2001/0048891 A1* | 12/2001 | McGeorge | ................ | A61L 2/10 422/22 |
| 2002/0074003 A1* | 6/2002 | Carroll | .................. | C09D 11/50 128/897 |
| 2002/0146343 A1* | 10/2002 | Jenkins | ..................... | A61L 2/24 422/24 |
| 2003/0017073 A1* | 1/2003 | Eckhardt | ................... | A61L 2/10 422/24 |
| 2009/0045352 A1* | 2/2009 | Morita | ..................... | C02F 1/32 250/474.1 |
| 2010/0034961 A1* | 2/2010 | Tenetov | ..................... | C09K 9/02 427/8 |
| 2011/0215054 A1* | 9/2011 | Lantis | ..................... | B65D 51/00 210/748.1 |
| 2013/0239874 A1* | 9/2013 | Smith | .................. | G01N 31/229 116/206 |
| 2013/0277574 A1* | 10/2013 | Dayton | ..................... | A61L 2/10 250/455.11 |
| 2014/0212332 A1* | 7/2014 | Bergman | ..................... | A61L 2/10 422/24 |
| 2015/0060696 A1 | 3/2015 | Dayton | | |
| 2015/0314637 A1* | 11/2015 | Kobayashi | ................. | C09J 4/00 401/192 |
| 2015/0343102 A1* | 12/2015 | Romo | ..................... | A61L 2/10 422/3 |

* cited by examiner

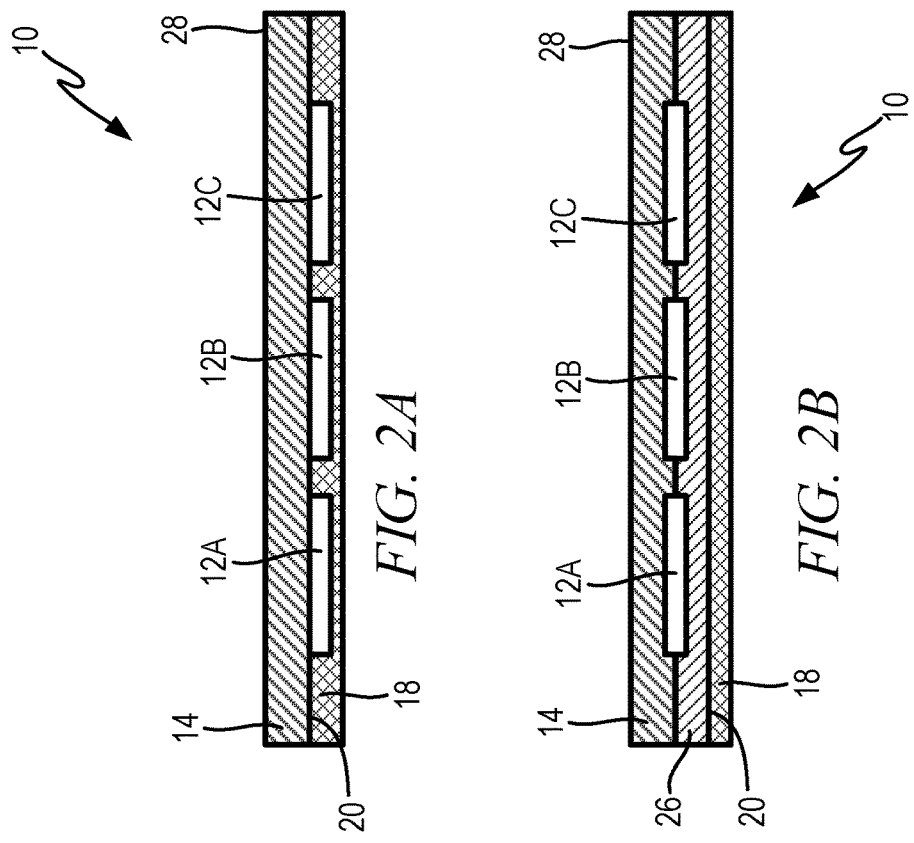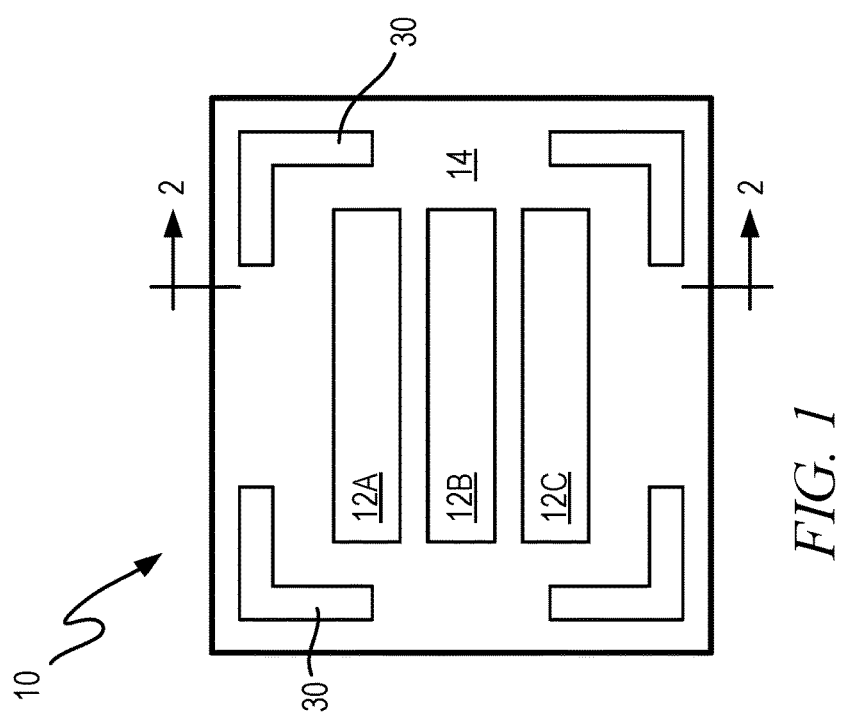

PHOTOCHROMIC INDICATOR AND A METHOD OF DOCUMENTING DECONTAMINATION OF AN OBJECT USING A PHOTOCHROMIC INDICATOR

BACKGROUND OF THE INVENTION

1. Field of the Invention

This application relates generally to a method and apparatus for documenting decontamination of an object and, more specifically, a photochromic indicator and method of using a photochromic indicator to determine whether a decontamination process was successfully performed.

2. Description of Related Art

Objects located in patient rooms, examination rooms and other locations within healthcare facilities, as well as in hotel rooms and other public places can be exposed to contagious pathogens from infected occupants. Certain pathogens have the ability to remain viable on the surfaces of such objects, able to infect subsequent occupants of the rooms who come into contact with the pathogens for extended periods of time. In an effort to prevent infections resulting from the presence of these pathogens, the surfaces of the objects are exposed to a decontaminating agent that at least deactivates (e.g., interferes with the pathogens' ability to perform certain cellular functions required to proliferate and cause an infection) any pathogens present, thereby rendering the objects pathogen reduced.

Traditionally, a liquid decontaminating agent was applied to the surfaces of the objects to be rendered pathogen reduced. To be effective, the decontaminating agent must remain wet on the surfaces for a minimum period of time. When decontaminating many surfaces in a room, however, the person applying the decontaminating agent may lose track of what surfaces have been treated. Further, since the decontaminating agent may be difficult to observe on the surfaces, the person may not be readily able to determine how long the decontaminating agent remained wet on each surface.

More recently, systems have been developed to decontaminate several surfaces in a room by exposing those surfaces to short-wavelength ultraviolet ("UVC") light, typically at wavelengths within a range from about 250 nm to about 260 nm. To be effective, however, an unobstructed line of sight must be established between the UVC source and the surfaces to be rendered pathogen reduced by the UVC light. The surfaces must also be exposed to the UVC light for a minimum length of time to achieve the desired level of decontamination. Any shadows or interruptions in the operation of the UVC light source could result in inadequate decontamination of the objects, thereby exposing later occupants of the room to infectious pathogens. But since the room must be unoccupied while the UVC light source is operational, the extent to which the decontamination process was performed toward completion is not personally monitored.

BRIEF SUMMARY OF THE INVENTION

Accordingly, there is a need in the art for an apparatus and method for validating complete performance of a decontamination process to achieve a desired level of pathogen reduction. The apparatus and method can optionally utilize a reversible photochromic indicator that exhibits a visible response to receiving a predetermined minimum exposure to UVC light. The photochromic indicator can also optionally be applied to surfaces to be decontaminated, and/or protected by a layer of material that is substantially transparent to UVC light. This protective layer 14 can permit application of a liquid decontaminating agent or other cleanser to the exposed surface of the protective layer 14 for topical cleaning of that exposed surface between decontamination processes utilizing UVC light.

According to one aspect, the subject application involves an apparatus for indicating minimum exposure of a surface to UVC light emitted by a source during a decontamination process. The apparatus includes a photochromic material to be applied to, or applied adjacent to the surface. The photochromic material is to exhibit a visible response to receiving the minimum exposure to the UVC light, and exhibit the visible response to a lesser extent after the photochromic material ceases to be exposed to the UVC light emitted by the source. A protective layer of material that is substantially transparent to the UVC light emitted by the source is positioned over the photochromic material to be disposed between the source and the photochromic material during the decontamination process.

According to another aspect, the subject application involves a method of evaluating progress of a decontamination process. The method includes applying a photochromic indicator to a surface to be rendered pathogen reduced during the decontamination process. This photochromic indicator includes a photochromic material that exhibits a visible response to being minimally exposed to UVC light, and exhibits the visible response to a lesser extent after the photochromic material ceases to be exposed to the UVC light. The photochromic material is exposed to the UVC light impinging on the surface during the decontamination process for a length of time expected to be suitable for achieving pathogen reduction of the surface to a desired extent during the decontamination process. After expiration of the length of time, an extent to which the decontamination process was completed is determined based on whether the photochromic material exhibits the visible response.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein:

FIG. 1 shows a front view of a photochromic indicator in accordance with an illustrative embodiment;

FIG. 2A shows a sectional view of an embodiment of the photochromic indicator taken along line 2-2 of FIG. 1;

FIG. 2B shows a sectional view of another embodiment of the photochromic indicator taken along line 2-2 of FIG. 1;

DETAILED DESCRIPTION OF THE INVENTION

Figure 3:
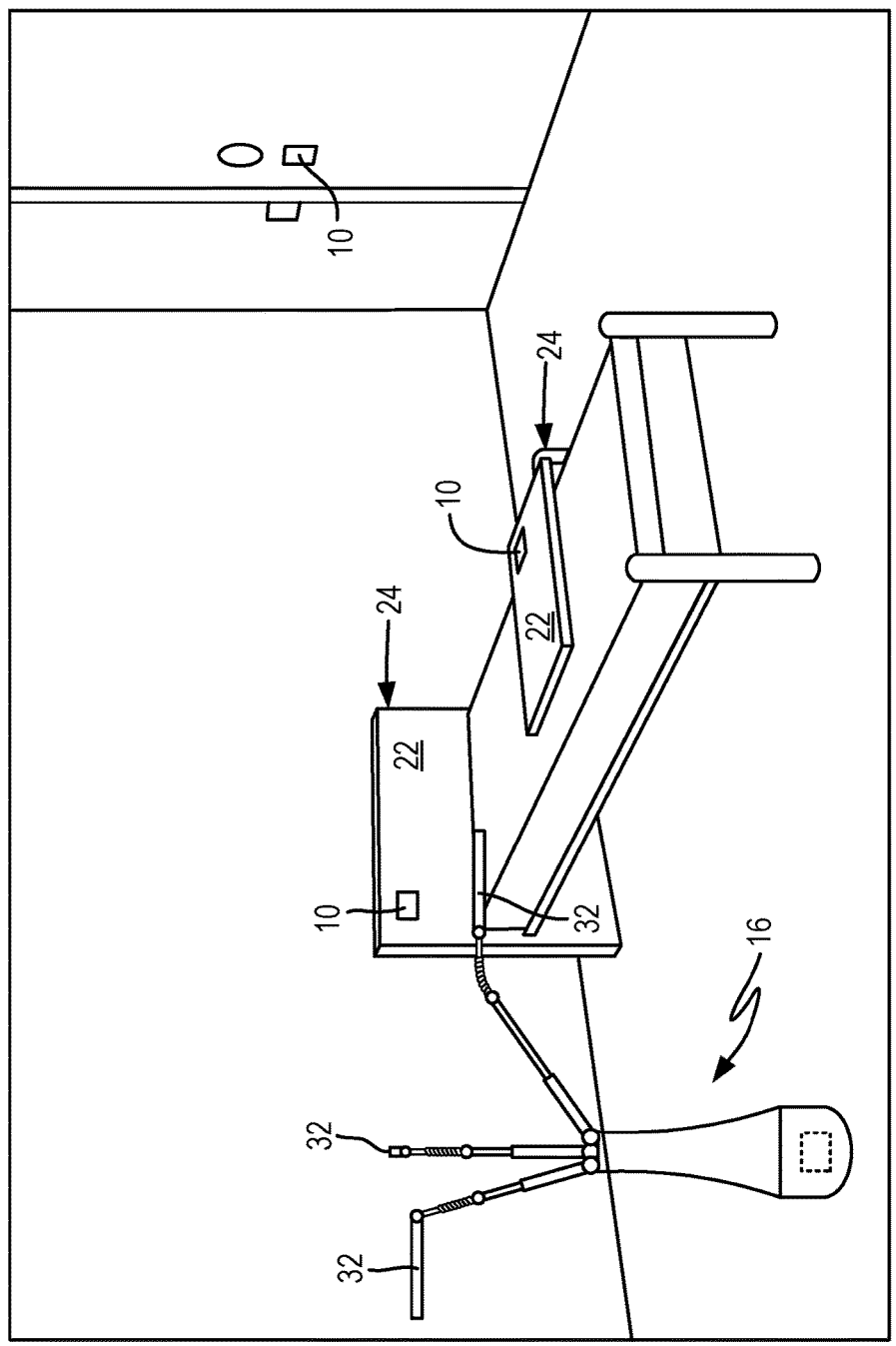
FIG. 3 shows an illustrative embodiment of a room in which a source of UVC light is located to decontaminate a plurality of surfaces, each provided with a photochromic indicator.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

An illustrative embodiment of a photochromic indicator 10 for indicating minimum exposure of a surface to UVC light emitted by a source 16 (FIG. 3) during a decontamination process is shown in FIG. 1. As shown, the photochromic indicator 10 includes at least one, and optionally a plurality of regions of photochromic material 12A, 12B, 12C (referred to generically herein as photochromic material 12) to be applied to, or applied adjacent to the surface 22 (FIG. 3) being exposed to the UVC light during a decontamination process to render that surface 22 pathogen reduced. The photochromic indicator 10 further includes an outer, protective layer 14 of material that is substantially transparent to the UVC light (e.g., allows transmission of at least 60% of the intensity of the UVC light, at least 70% of the intensity of the UVC light, at least 80% of the intensity of the UVC light, at least 90% of the intensity of the UVC light, and optionally up to 100% of the intensity of the UVC light) emitted by the source positioned over the photochromic material 12. This protective layer 14 is to be disposed between the source and the photochromic material 12 during the decontamination process. For the embodiment shown in FIG. 1, the protective layer 14 can be formed from UVC transmissive materials applied over the photochromic material 12. Examples of such UVC-transmissive materials are polypropylene (PP), low-density polyethylene (LDPE), or fluorinated ethylene propylene (FEP). Additionally, while PP, LDPE and FEP will allow UVC transmission, they will only do so with a small cross sectional thicknesses, such as 0.001 in., 0.002 in., 0.005 in., as examples of suitable cross-section thicknesses. However, the cross-section thickness of each region of photochromic material 12A, 12B, 12C can optionally be independently established to cause a plurality of the regions of photochromic material 12A, 12B, 12C, even if the plurality of regions are formed from the same photochromic material, to exhibit different visible responses to being exposed to the same quantity and/or intensity of UVC light. For example, and as discussed in detail below, two or more, or each of the regions of photochromic material 12A, 12B, 12C can optionally indicate increasing exposures to the UVC light. The thicker the cross section thickness, the greater the quantity of photochromic material that must be exposed to the UVC light to exhibit the visible response. In other words, relatively-thick regions of photochromic material 12A, 12B, 12C can be thought of as having a greater resistance to exhibiting the visible response, or a greater "photochromic mass," requiring a greater exposure to the UVC light before exhibiting the visible response than relatively-thin regions of photochromic material 12A, 12B, 12C. Thus, a different thickness can be established for two or more of the regions of photochromic material 12A, 12B, 12C provided to the photochromic indicator 10 to allow an observer to evaluate whether a sufficient dose of the UVC light was administered during a decontamination process to achieve the desired level of pathogen reduction, as defined below.

Being substantially transparent, the protective layer 14 allows transmission of at least 60%, or optionally at least 70%, or optionally at least 80%, or optionally at least 90%, and optionally up to 100% of the intensity of the UVC light emitted by the source.

As shown in the sectional view of FIG. 2A, the protective layer 14 can optionally include a pressure-sensitive adhesive 18 applied to an inward-facing surface 20 that opposes the surface 22 (FIG. 3) of an object 24 to which the photochromic indicator 10 is applied. For such embodiments, the photochromic material 12 can also be applied to the inward-facing surface 20 such that the adhesive-backed protective layer 14 sandwiches the photochromic material 12 between the surface 22 of the object 24 and the adhesive layer 18 provided to the inward-facing surface 20 of the protective layer 14, thereby holding the photochromic material 12 in place. According to alternate embodiments, the photochromic material 12 can be disposed between the inward-facing surface 20 of the protective layer 14 and the pressure-sensitive adhesive 18, as shown in FIG. 2A.

According to yet other embodiments, such as that shown in FIG. 2B, the photochromic indicator 10 can also optionally be provided with a backing layer 26 that is arranged on an opposite side of the photochromic material 12 relative to the protective layer 14. In other words, the photochromic material 12 can be disposed between the protective layer 14 and the backing layer 26, which can optionally include an inward-facing surface provided with a pressure-sensitive adhesive 18. The photochromic indicator 10 of the present embodiment can then be applied as a sticker, decal, label or placard to, or adjacent to the surface 22 to be rendered pathogen reduced during a decontamination process.

Yet other embodiments can optionally include a protective layer 14 formed from a static-cling material, that is devoid of the pressure-sensitive adhesive 18. For such embodiments, electrostatic attraction between the protective layer 14 and the surface 22 of the object 24 holds the photochromic indicator 10 in place.

The protective layer 14 can optionally be substantially transparent to visible light, allowing the underlying surface 22 of the object 24 and/or the optional underlying backing layer 26 to be viewed when observed through the outwardly-exposed surface 28 of the photochromic indicator 10. For embodiments including the backing layer 26, the backing layer 26 and optionally the adhesive 18 can also optionally be formed from materials that are substantially transparent to visible light. Likewise, the photochromic material 12 can also optionally be formed from a material that, prior to exposure to the UVC light, is substantially transparent to visible light. When all such materials provided to the photochromic indicator 10 are substantially transparent to visible light, the photochromic indicator 10 is minimally detectable at a casual glance on, or adjacent to the surface(s) to be rendered pathogen reduced. As shown in FIG. 1, corner identifiers 30 or some other type of visible identifier visible to an onlooker who is observing the photochromic indicator 10 can help to identify the location of the photochromic material 12. In FIG. 1, the four corner indicators 30 collectively frame the region where the observer can expect to find the photochromic material 12. This enables the onlooker inspecting the photochromic indicator 10 to determine degree to which the decontamination process was completed as described below, and readily determine the location of an under-exposed photochromic indicator 10 to conclude that a decontamination process did not achieve the desired level of pathogen reduction.

Rendering the surfaces "pathogen reduced" does not necessarily require the subject surfaces 22 to be 100% sterile, free of any and all living organisms that can viably reproduce. Instead, to be considered pathogen reduced, there must be a lower level of living contagions on the decontaminated surfaces capable of reproducing or otherwise causing an infection after performance of the decontamination process than the level that existed on the surfaces prior to performance of the decontamination process. For example, the exposed surfaces 22 in the room can be considered to be pathogen reduced if at least a 1 $\log_{10}$ reduction of such contagions on those surfaces 22 remain infectious (i.e., no more than 1/10th of the biologically-active contagions originally on the exposed surfaces 22 remain active or infectious at a time when the decontamination process is completed) occurs. According to yet other embodiments, the surfaces 22 can be considered pathogen reduced once at least a 3 $\log_{10}$ reduction (i.e., 1/1,000th) of such contagions on the surfaces 22 is achieved.

As shown in FIG. 3, the source 16 includes one or a plurality of UVC bulbs 32 that direct UVC light having a wavelength within a range from about 250 nm to about 260 nm toward various surfaces 22 to be decontaminated, and thereby rendered pathogen reduced. For the illustrative embodiment shown in FIG. 3, various different surfaces 22 are each provided with a photochromic indicator 10 to be rendered pathogen reduced. Those surfaces 22 in FIG. 3 include at least one surface 22 of the each of the following objects 24: patient bed, tray table and door. However, it is to be understood that the photochromic indicator 10 can be applied to one surface 22 of interest, or a plurality of surfaces 22, including those shown in FIG. 3, and/or other surfaces 22 not expressly identified herein or shown in FIG. 3 without departing from the scope of the present disclosure.

The photochromic material 12 can be formed from any composition, compound, combination or other material, such as materials based on spiropyrans, spirooxazines, and diarylethenes, for example. According to specific embodiments, examples of the spiropyran-based photochromic materials include, but are not limited to:

1-(2-Hydroxyethyl)-3,3-dimethylindolino-6'-nitrobenzopyrylospiran
1,3,3-Trimethylindolinobenzopyrylospiran;
1,3,3-Trimethylindolino-6'-nitrobenzopyrylospiran;
1,3,3-Trimethylindolino-6'-bromobenzopyrylospiran;
1,3,3-Trimethylindolino-8'-methoxybenzopyrylospiran;
1,3,3-Trimethylindolino-β-naphthopyrylospiran; and
1,3,3-Trimethylindolinonaphthospirooxazine.

According to other specific embodiments, examples of the spirooxazine-based photochromic materials include, but are not limited to:

2,3-Dihydro-2-spiro-4'-[8'-aminonaphthalen-1'(4'H)-one] perimidine; and
2,3-Dihydro-2-spiro-7'-[8'-imino-7',8'-dihydronaphthalen-1'-amine]perimidine.

According to other specific embodiments, examples of the diarylethene-based photochromic materials include, but are not limited to:

2,3-Bis(2,4,5-trimethyl-3-thienyl)maleic Anhydride;
2,3-Bis(2,4,5-trimethyl-3-thienyl)maleimide;
cis-1,2-Dicyano-1,2-bis(2,4,5-trimethyl-3-thienyl)ethane;
1,2-Bis[2-methylbenzo[b]thiophen-3-yl]-3,3,4,4,5,5-hexafluoro-1-cyclopentene; and
1,2-Bis(2,4-dimethyl-5-phenyl-3-thienyl)-3,3,4,4,5,5-hexafluoro-1-cyclopentene.

Of course, the exemplary photochromic materials listed above do not constitute an exhaustive listing of all suitable photochromic materials 12 encompassed by the scope of the present application. Rather, any photochromic material 12 that exhibits a visible response to receiving the minimum exposure of the UVC light to achieve a desired, predetermined minimum level of pathogen reduction, and subsequently exhibits the visible response to a lesser extent (e.g., returns to its original appearance prior to being exposed to the UVC light) after the photochromic material 12 ceases to be exposed to the UVC light emitted by a UVC light source 16 (FIG. 3) during a decontamination process, is considered within the scope of the present application. Further, the photochromic material 12 can optionally be selected to continuously exhibit the visible response for a length of time (e.g., at least 2 minutes, at least 4 minutes, at least 6 minutes, at least 8 minutes, at least 10 minutes, at least 15 minutes, etc.) after the photochromic material 12 ceases to be exposed to the UVC light from the source. Accordingly, following expiration of the time expected to be required to complete a decontamination process, the person conducting the decontamination process can enter the room once the source has been deactivated. Since the photochromic material 12 for such an embodiment continues to exhibit the visible response to reaching the minimum exposure of UVC light, the person can look around the room and visibly determine whether the decontamination process successfully exposed the surfaces to be decontaminated with the requisite dose of UVC light to achieve the desired level of pathogen reduction.

Each region of photochromic material 12A, 12B, 12C provided to a photochromic indicator 10 can optionally be independently selected to exhibit the same visible response to be exposed to UVC light for purposes of redundancy. According to such embodiments, the regions of photochromic material 12A, 12B, 12C can be selected to change color, exhibit a variable opacity, etc. once those regions of photochromic material 12A, 12B, 12C have been suitably exposed to the UVC light to ensure the desired level of pathogen reduction has been achieved. Thus, if a first region of photochromic material 12A is damaged or otherwise ceases to exhibit the correct response to receiving the minimum exposure to the UVC light, a visible response by the other regions of photochromic material 12B, 12C in FIG. 1 could be relied upon to determine that the decontamination process was successfully completed for that surface 22.

According to alternate embodiments, each of the regions of photochromic material 12A, 12B, 12C can optionally exhibit different visible responses (e.g., turn different colors, exhibit different levels of opacity, etc.) to being exposed to the UVC light. For example, if exposure of a surface 22 to UVC light is prematurely terminated too early to achieve the desired level of pathogen reduction, if the light source 16 is positioned too far away from a surface 22 that is being decontaminated, or if another condition is present that results in a lesser level of pathogen reduction of the surface 22 from that desired, a first region of photochromic material 12A may exhibit a first visible response, while a second region of photochromic material 12B exhibits a different visible response. Likewise, a third region of photochromic material 12C can also optionally exhibit yet a third, different visible response. According to such embodiments, the progress of the decontamination process can be estimated based on the differing visible responses. For instance, at least a 1 $\log_{10}$ pathogen reduction of the corresponding surface 22 has been achieved, but the decontamination process did not achieve at least a 3 $\log_{10}$ pathogen reduction of that surface 22 provided with the photochromic indicator 10.

The different visible responses exhibited by a plurality of the regions of photochromic material 12A, 12B, 12C can be achieved by forming each of the plurality of regions exhibiting the different visible response from a different photochromic material. According to alternate embodiments, the plurality of different regions of photochromic material 12A, 12B, 12C can be formed with different thickness of the same material as described above, or with different thicknesses of different photochromic materials.

For each of these embodiments, the photochromic material(s) 12 can be selected to have properties that cause the photochromic material 12 to exhibit the visible response as a function of the desired level of pathogen reduction to be indicated. In other words, the photochromic material 12 can be application specific, or can be standardized to indicate that a decontamination process has resulted in at least a 1 $\log_{10}$ pathogen reduction of the corresponding surfaces 22, or at least a 3 $\log_{10}$ pathogen reduction.

In use, a photochromic indicator 10 can be applied to a surface 22, or multiple surfaces 22 of each object 24 that is to be decontaminated. The photochromic indicator 10 can optionally be applied directly to the surface(s) 22, or applied adjacent to the surface(s) at a position where it is reasonable to assume UVC light impinging on the photochromic indicator 10 is impinging on the surface(s) 22. In FIG. 3, a photochromic indicator 10 has been applied to the surface 22 of the headboard of the bed, the top surface 22 of the tray table, and an interior surface 22 of the entry door, but other surfaces 22 within the room can also be provided with the photochromic indicator 10 without departing from the scope of the present application.

Each of the photochromic indicators 10 applied to the surface(s) 22 in the room can optionally be left in place for use during multiple decontamination processes, or can be disposable to be replaced after a predetermined period of time (e.g., every month, every year, etc.) or after a predetermined number of decontamination processes have been performed (e.g., every 10, or 100 decontamination processes, etc.). Between decontamination processes however, the outwardly-exposed surface 28 of the protective layer 14 can optionally be decontaminated by topical application of a liquid decontaminating agent or otherwise cleaned with a soap or other detergent, water, etc., since the photochromic material 12 is protected by the protective layer 14.

With the photochromic indicator(s) 10 in place, the UVC light source 16 can be positioned within the room and configured to emit the UVC light for a period of time expected to be appropriate to achieve a desired level of pathogen reduction on each of the surfaces 22. The UVC light source 16 can optionally be stationary within the room during the decontamination process, concurrently broadcasting the UVC light to each surface 22 to be decontaminated. However, since the UVC light source 16 will be separated from different surfaces 22 by different distances and establish different angles of impingement of the UVC light on the different surfaces 22, the different surfaces 22 may each require a different length of exposure to the UVC light for that decontamination process to successfully achieve the desired level of pathogen reduction on each surface 22. Accordingly, the UVC light source 16 is to be configured to emit the UVC light at least as long as expected to achieve the desired level of pathogen reduction on the surface 22 requiring the longest exposure time to achieve the desired level of pathogen reduction.

According to other embodiments, the UVC light source 16 can be automated to reposition itself to emit UVC light from a plurality of locations within the room during a decontamination process, and/or automated to adjust a direction in which UVC light is emitted within the room during a decontamination process. For such embodiments, the the UVC light source 16 is to be configured to emit the UVC light for the time expected to achieve the desired level of pathogen reduction of the surface(s) 22 during each phase (e.g., for each location and/or emission direction) of the decontamination process. The photochromic material 12 can optionally be chosen to maintain its visible response at least as long as required for emission of the UVC light at each of the locations and/or in each of the emission directions.

Regardless of the configuration of the UVC light source 16, the UVC light source 16 is activated to emit the UVC light while there are no occupants in the room. As each photochromic indicator 10 is exposed to the UVC light, it will exhibit its visible response after being exposure to the minimum exposure level expected to achieve the level of pathogen reduction desired for the corresponding surface(s) 22.

Following completion of the decontamination process, the UVC light source 16 is deactivated to terminate emission of the UVC light. The photochromic material 12 of each photochromic indicator 10 maintains its visible state when the UVC light ceased to be impinged on the respective photochromic indicator 10 for at least a minimum period of time (e.g., 10 minutes). Afterwards, the person responsible for the decontamination process re-enters the room and inspects each photochromic indicator 10 provided to a surface 22 that was to be rendered pathogen reduced. Based on whether the photochromic material 12 of each photochromic indicator 10 exhibits its respective visible response, it can be determined whether the decontamination process was successfully completed. In the event one or more photochromic indicators 10 indicates that the desired level of pathogen reduction has not been achieved, the decontamination process can be repeated in its entirety, but with a longer emission time for the entire decontamination process, or at least for each location and/or emission direction that did not achieve the desired level of pathogen reduction.

Figure 4:
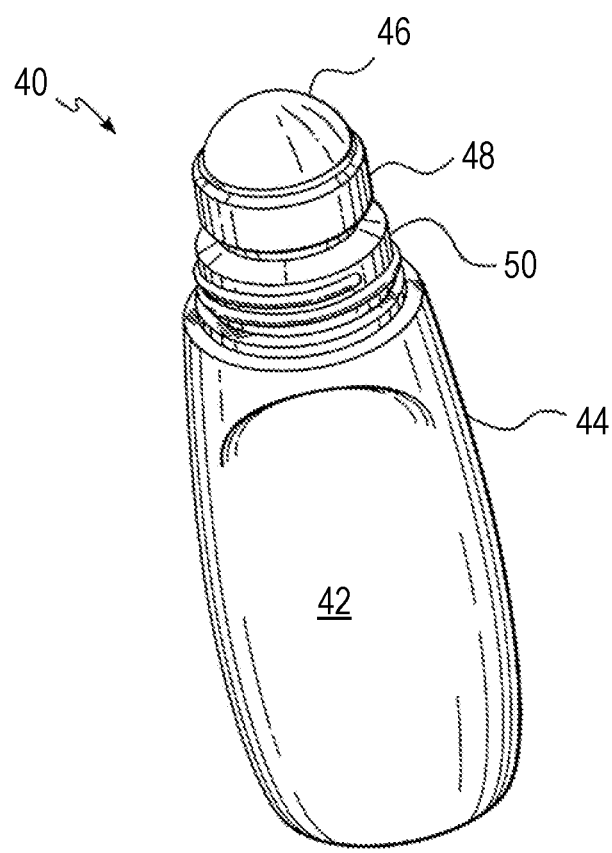
FIG. 4 shows an illustrative embodiment of an applicator for applying photochromic material directly to a surface.

Instead of, or in addition to being provided to a substrate to be applied as a label, sticker, decal, etc. onto, or near the surface to be decontaminated as described above, the photochromic material 12 can also be applied in a liquid, gel, paste, powder coating, or other form by itself, separate from any supporting substrate and/or protective layer. For instance, the liquid, gel or other form of photochromic material 12 can be disposed within a reservoir 42 defined by a housing 44 of a roll-on applicator 40 such as that shown in FIG. 4. When the roll-on applicator 40 is inverted, the force of gravity urges the photochromic material 12 towards a ball 46 that is rollably supported in a socket 48 that is in fluid communication with the reservoir 42. An interior surface of the ball 46 is coated with the photochromic material 12. As the ball is rolled over a surface that is to be decontaminated or located near a surface to be decontaminated, however, the coated surface of the ball 46 is rotated to make contact with the surface, thereby depositing the photochromic material 12 that was coating the ball 46 onto that surface. To prevent the roll-on applicator 40 from drying out, external threading 50 or other releasable (e.g., allows for repeated attachment and removal without damage) fastener is compatible with a mating feature provided to a cap, not shown, that conceals the ball 46 when not in use.

The photochromic material 12 in the roll-on application 40 can be reactive to UVC light, and/or optionally reactive to more than UVC light to exhibit a visible response. For example, the photochromic material 12 can optionally be combined with a second material that exhibits a visible response (e.g., change in color, opacity, exhibit a luminescence, etc.) when exposed to a stimulant other than UVC. Specific examples of the second material include, but are not limited to: fluorescent paints, dyes, inks, detergents, and other substances that, when exposed to long-wave (e.g., wavelengths within a range from about 315 nm to about 400 nm) ultraviolet ("UVA") light emitted by so-called "black lights" or "blacklight blue" lights, fluoresce.

Use of the roll-on applicator 40 with the photochromic material 12 to evaluate the success of a decontamination process is similar to the use of the applied photochromic indicator 10 described above. A person could roll the photochromic material 12 in the roll-on applicator 40 directly onto a surface 22 to be decontaminated, or onto another surface near the surface to be decontaminated to avoid potentially shielding pathogens on the surface to be decontaminated with the photochromic material 12. The UVC source 16 would then be used as described above to emit UVC light onto the surface(s) 22 marked with the rolled-on photochromic material 12. Following completion of the UVC exposure process, the person could re-enter the room and observe whether the photochromic material 12 applied to one or more surfaces 22 is exhibiting the visible response, and form a conclusion about whether the decontamination process achieved the desired level of pathogen reduction.

For embodiments involving a combination of the photochromic material 12 and a second material, such as a fluorescent material that fluoresces when illuminated with UVA light, additional methods of evaluating the success of a decontamination process are available. Again, the same method such as that previously described utilizing a roll-on applicator filled with the photochromic material 12 can be performed. The concentration of the second material in the combination should be selected to avoid interfering with the visible reaction exhibited by the photochromic material 12, alone, in response to being exposed to UVC light to an extent that would make observation of such a visible response difficult to observe with the naked eye. The roll-on applicator can be used to apply the combination of photochromic material 12 and the second material (hereinafter "Combination Material") directly to the surface(s) 22 to be decontaminated, or directly to other surface(s) near the surface(s) 22 to be decontaminated. For example, the Combination Material can be applied directly to the uppermost surface of the headboard of the bed instead of a portion of the headboard near where the patient's head is to be located. Pathogens are less likely to be present on this uppermost surface than at a location near where the patient's head rests, and a subsequent patient in the bed is less likely to encounter the uppermost surface of the headboard. However, the uppermost surface of the headboard is close enough to the surface 22 to be decontaminated that it is reasonable to conclude that if the uppermost surface receives a sufficient dose of UVC light to be considered successfully decontaminated, so did the surface 22, since that surface 22 is likely a greater focus of the decontamination process. As such, it was likely to be more-directly targeted with the UVC light than the uppermost surface of the headboard and, presumably, received an even greater dose of the UVC light.

However, the concentration of the second material present in the Combination Material should be at least sufficient to allow the combination of the second material and the photochromic material 12 to noticeably (e.g., with the naked eye) fluoresce in response to being exposed to UVA light. Using a roll-on applicator 40 filled with such a combination allows for another embodiment of a method for evaluating the effectiveness of a decontamination process. According to the present embodiment, the person who is to manually decontaminate the surface(s) 22 (or another person who is to audit the effectiveness and thoroughness of the decontamination process) can directly apply the Combination Material onto the surface(s) 22, or onto nearby surface(s) close to the surface(s) 22 to be decontaminated. If the auditor applied the Combination Material, the specific locations where the Combination Product was applied is unknown to the person conducting the manual decontamination process. Thus, the person conducting the decontamination process is motivated to thoroughly decontaminate all possible surfaces (22) where the Combination Product was likely applied. During the manual decontamination process, the person applies a liquid or other manually-applied disinfectant to the various surfaces 22 throughout the room in accordance with the instructions for that disinfectant to achieve the desired level of pathogen reduction. Following completion of the manual decontamination process, the auditor (or cleaner) can re-enter the room and activate a black light that emits UVA light and look for any visible fluorescence. Since the Combination Material can be removed from the surfaces 22 by the disinfectant, a lack of fluorescence from a location on a surface 22 where the Combination Material was applied indicates that that particular surface 22 was suitably decontaminated to achieve the desired level of pathogen reduction thereon. However, if that location where the Combination Material was applied fluoresces, it can be presumed that that particular surface 22 was not thoroughly decontaminated to achieve the desired level of pathogen reduction thereon.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus for indicating exposure of a surface to at least a predetermined dose of UVC light emitted by a source during a decontamination process, the apparatus comprising:
    a photochromic material to be applied to, or applied adjacent to the surface, wherein the photochromic material exhibits a visible response to receiving the predetermined dose of the UVC light and, after the photochromic material ceases to be exposed to the UVC light emitted by the source, an appearance of the photochromic material returns to an original appearance that was visible before exposure of the photochromic material to the UVC light;

a second material that exhibits a visible response to being exposed to light having a wavelength outside of range of wavelengths constituting UVC light; and a protective layer of material that is substantially transparent to the UVC light emitted by the source positioned over the photochromic material to be disposed between the source and the photochromic material during the decontamination process.

2. The apparatus of claim 1, wherein the photochromic material is substantially transparent before being exposed to the UVC light and is substantially opaque and/or changes color as the visible response to receiving the predetermined dose of the UVC light.

3. The apparatus of claim 1 further comprising a second photochromic material that exhibits a different visible response than the visible response of the photochromic material to indicate different exposures to the UVC light.

4. The apparatus of claim 1, wherein the visible response of the photochromic material is visibly perceptible by an observer for at least a predetermined period of time after the photochromic material ceases to be exposed to the UVC light emitted by the source.

5. The apparatus of claim 4, wherein the predetermined period of time comprises at least four minutes.

6. The apparatus of claim 4, wherein the predetermined period of time comprises at least ten minutes.

7. The apparatus of claim 1 further comprising a visible identifier that indicates a general vicinity of the photochromic material in an original state before the photochromic material exhibits the visible response.

8. The apparatus of claim 1 further comprising an adhesive that adheres the apparatus to the surface.

9. The apparatus of claim 1 further comprising a backing layer, wherein the photochromic material is disposed between the backing layer and the protective layer.

10. A method of evaluating progress of a decontamination process, the method comprising:

applying a photochromic indicator to a surface to be rendered pathogen reduced during the decontamination process, the photochromic indicator comprising a photochromic material that exhibits a visible response to being exposed to at least a predetermined dose of UVC light and, after the photochromic material ceases to be exposed to the UVC light, an appearance of the photochromic material returns to an original appearance that was visible before exposure of the photochromic material to the UVC light;

applying a second material that exhibits a visible response to being exposed to light having a wavelength outside of a range of wavelengths constituting UVC light adjacent to the photochromic indicator;

exposing the photochromic material to the UVC light impinging on the surface during the decontamination process for a length of time expected to be suitable for achieving pathogen reduction of the surface to a desired extent during the decontamination process; and after expiration of the length of time, using a light source that emits the light with the wavelength outside of the range of wavelengths constituting UVC light to cause the second material to exhibit the visible response, and determining an extent to which the decontamination process was completed based on whether the photochromic material exhibits the visible response.

11. The method of claim 10, wherein said determining the extent to which the decontamination process was completed comprises observing a plurality of photochromic materials provided to the photochromic indicator, and making a determination of the extent to which the decontamination process was completed based on a different visible response exhibited by each of the plurality of photochromic materials.

12. The method of claim 10, wherein said determining comprises making a determination, based on the visible response, that the desired level of pathogen has not been achieved, and said method further comprises reactivating a source of the UVC light to achieve the desired level of pathogen reduction.

13. The method of claim 10, wherein the second material is combined with the photochromic material and applied concurrently with application of the photochromic material.

* * * * *